(12) United States Patent
Schmidt

(10) Patent No.: US 8,594,960 B2
(45) Date of Patent: Nov. 26, 2013

(54) METHOD FOR DETERMINING AN ATTENUATION MAP

(75) Inventor: Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 926 days.

(21) Appl. No.: 12/458,431

(22) Filed: Jul. 13, 2009

(65) Prior Publication Data

US 2010/0010757 A1 Jan. 14, 2010

(30) Foreign Application Priority Data

Jul. 14, 2008 (DE) .................. 10 2008 032 996

(51) Int. Cl.
*G01R 13/02* (2006.01)

(52) U.S. Cl.
USPC .......................................... 702/67

(58) Field of Classification Search
USPC ......... 702/57, 66, 67, 70, 115, 129, 134, 173, 702/179, 183; 382/274
See application file for complete search history.

(56) References Cited

U.S. PATENT DOCUMENTS

| 5,345,381 | A * | 9/1994 | Wallschlaeger ............... 378/15 |
| 5,999,588 | A | 12/1999 | Shao et al. |
| 6,455,858 | B1 | 9/2002 | Gagnon |
| 6,740,883 | B1 | 5/2004 | Stodilka et al. |
| 7,327,138 | B2 | 2/2008 | Krieg et al. |
| 7,859,261 | B2 | 12/2010 | Jattke et al. |
| 2003/0053597 | A1 * | 3/2003 | Flohr et al. ................. 378/156 |
| 2006/0058641 | A1 | 3/2006 | Krieg et al. |
| 2006/0237652 | A1 | 10/2006 | Kimchy et al. |
| 2007/0237288 | A1 * | 10/2007 | Tkaczyk et al. ............... 378/5 |
| 2008/0135769 | A1 | 6/2008 | Rosen |
| 2008/0231275 | A1 | 9/2008 | Jattke et al. |
| 2009/0105583 | A1 | 4/2009 | Martin et al. |
| 2009/0135998 | A1 * | 5/2009 | Rossl et al. ................. 378/98 |

FOREIGN PATENT DOCUMENTS

| DE | 10 2004 043 889 | 3/2006 |
| DE | 102004043889 A1 | 3/2006 |
| DE | 102007013564 A1 | 9/2006 |
| DE | 10 2006 033 383 | 1/2008 |
| DE | 102006033383 A1 | 1/2008 |
| DE | 102007021932 A1 | 11/2008 |
| DE | 102007044860 A1 | 12/2008 |
| DE | 102007044874 A1 | 4/2009 |
| EP | 1105750 B1 | 10/2004 |
| WO | WO2008138822 A1 | 11/2008 |

OTHER PUBLICATIONS

Abstract of WO 2008/006451 published Jan. 17, 2008.

* cited by examiner

*Primary Examiner* — Mohamed Charioui
(74) *Attorney, Agent, or Firm* — Harness, Dickey & Pierce

(57) ABSTRACT

A method is disclosed for defining an attenuation map. In at least one embodiment, the method includes creating at least two data sets from which attenuation values are able to be determined; evaluating the data sets and determining attenuation values; weighting the attenuation values determined and creating the attenuation map by inserting the weighted attenuation values.

17 Claims, 2 Drawing Sheets

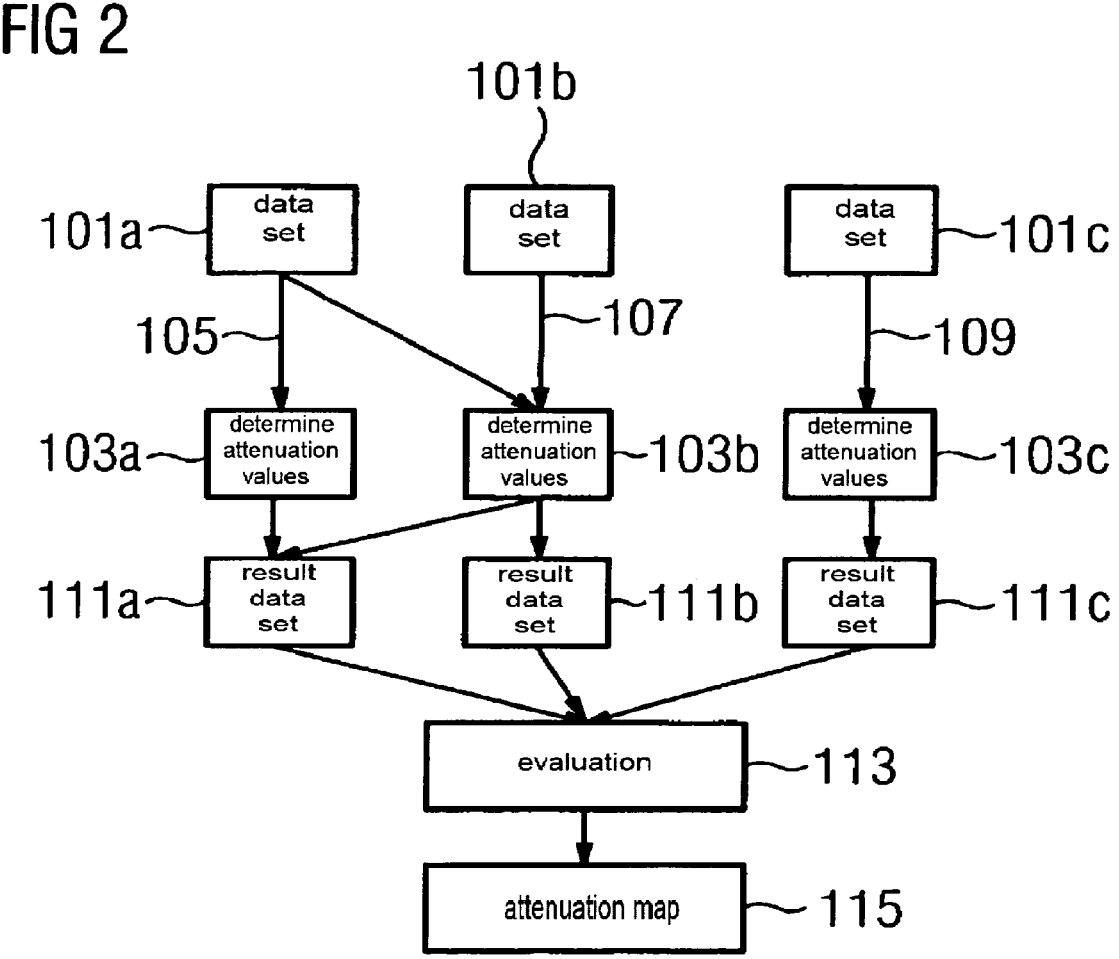

METHOD FOR DETERMINING AN ATTENUATION MAP

PRIORITY STATEMENT

The present application hereby claims priority under 35 U.S.C. §119 on German patent application number DE 10 2008 032 996.7 filed Jul. 14, 2008, the entire contents of which are hereby incorporated herein by reference.

FIELD

At least one embodiment of the present invention generally relates to a method for determining an attenuation map.

BACKGROUND

As well as Magnetic Resonance tomography (MR), Positron Emission Tomography (PET) is becoming increasingly widely used in medical diagnosis. While MR involves an imaging method for representing structures and sectional images within the body, PET makes possible a visualization and quantification of metabolism activities in-vivo.

PET uses the particular properties of positron emitters and positron annihilation in order to determine quantitatively the function of organs or cell areas. In such cases the appropriate radiopharmaceuticals which are marked with radio nuclides are administered to the patient. As they decay, the radio nuclides emit positrons which after a short distance interact with an electron, which causes what is referred to as an annihilation to occur. During this process two Gamma quanta occur which fly off in opposite directions (displaced by 180°). The Gamma quanta are detected by two opposite PET detector modules within a specific time window (coincidence measurement), by which the location of the annihilation is determined to a position on the connecting line between these two detector modules.

For verification the detector module must generally cover a large part of the gantry arc length for PET. It is divided up into detector elements with sides of a few millimeters in length in each case. On detection of a Gamma quantum each detector element generates an event recording which specifies the time as a well as the verification location, i.e. the corresponding detector element. This information is transferred to a fast logic and compared. If two events coincide in a maximum time interval then it is assumed that a Gamma decay process is occurring on the connecting line between the two corresponding detector elements. The PET image is reconstructed with a tomography algorithm, i.e. what is referred to as back projection.

The combination of PET with other tomographic methods, especially computer tomography (CT) is known. Combined PET-CT devices typically allow the deficient local resolution of PET systems to be compensated for. At the same time CT offers a presentation of the anatomy of the patient so that, on superimposition of the CT and PET data, it can be established precisely where in the body the PET activity has taken place. With combined PET-CT devices a PET device and a CT device are typically arranged behind one another so that within an examination the patient can be moved seamlessly from one device into the other one. The two measurements can then take place directly consecutively.

A combination of a PET device with an MR device is advantageous since MR gives a higher soft tissue contrast by comparison with CT. Combined MR-PET systems are already known in which the PET detectors are arranged within an opening defined by the MR magnets with gradient system and excitation coil. In such cases they are positioned next to the excitation coil so that the examination volumes of the MR and PET system do not coincide but are offset in the Z direction. Consequently, like the PET-CT system, PET and MR data cannot be measured simultaneously.

In such cases it is especially to be preferred that the PET device be arranged within the MR device and that the two examination volumes are superimposed. In this case both morphological MR data and also PET data can be determined within one measurement run. As well as the effect of time-saving the two image data records can be shown superimposed in a simple manner so that a diagnosis is simplified for the doctor.

For integration of the PET and MR device it is necessary to arrange the PET detectors within the MR device, so that the imaging volumes lie isocentrically. For example the PET detectors can be arranged on a support structure (support bar, gantry) within the MR device. This can for example be 60 detectors in a ring-shaped arrangement on the support bar. For each of the detectors, which can also be combined into detector blocks, a cooling connection and electrical supply leads are required. These are likewise to be arranged in the MR device. In addition a number of signal processing units is required which are likewise arranged in the MR device. These are connected via the electrical leads to the detectors and are used for signal processing.

In the event of the combination of MR and PET in a combined system an attenuation of the Gamma quanta occurs because of everything which lies between the point of origination of the respective Gamma quanta and the PET detector. In the reconstruction of PET images this attenuation must be taken into account in order to prevent image artifacts. Between the point of origination of the Gamma quant in the body of the patient and the verifying PET detector lies on the one hand patient tissue, generally air and a part of the MR-PET system itself, for example cladding of the patient opening or a patient bed. The attenuation values of the components or accessory parts to be taken into account are combined into attenuation maps $\mu$. In such cases and attenuation map contains attenuation values for each volume element (voxel) of the investigated volume. Thus for example an attenuation map can be created for the patient table. The same typically applies to local coils applied to the patient for MR examinations. To create the attenuation map it is necessary to determine and to collect together the attenuation values. The values can typically be determined by CT imaging or by a PET transmission measurement of the respective component. These types of attenuation maps can be measured once since the attenuation values do not change over the lifetime of the respective component. For attenuation correction large differences in the attenuation between the different tissue, above all soft parts and bones, are primarily of significance.

With PET-CT systems it is known that an attenuation map can be calculated from CT images using the x-ray absorption coefficients and used for the attenuation correction of PET data. This can also be employed in the measurement of attenuation values of the components. With PET systems a direct determination of the attenuation map from the actual measurement data is not possible. Measurements must thus be made in test measurements with homogeneous PET phantoms, so that the intensity of the Gamma quanta arising is known. Alternately the use of x-ray sources with PET systems is known which are moved around the patient. By detecting the radiation of these radiation sources the attenuation is determined, but this is time-consuming.

With MR-PET systems it is desirable to be able to determine the attenuation directly from MR data sets. Such methods are already known.

Thus a method is known from DE 10 2004 043 889 A1 for creating a nuclear medical image. The image is produced from a data set comprising both data of a magnetic resonance examination and also of a PET measurement. A reference MR data set of the area for which the image is to be recorded of a reference patient with an associated correction data set is provided. A transformation which maps the reference MR data set to the MR image is created and applied to the correction data set for creating a transformed correction data set which is registered with the nuclear medical data set. This involves an Atlas-based method for determining the attenuation values which, with the assistance of the measured MR image, are transferred to the PET data set and used for attenuation correction.

A method is known from DE 10 2006 033 383 A1 for determining an attenuation map for a living being. Attenuation values are able to be predicted on the basis of an MR data set by means of a trained algorithm.

In a further known method specific MR sequences are used in order for example to make bones or plastic parts and coils visible. After a segmentation and registration with PET data, attenuation values can be assigned to the corresponding regions. It is likewise known that the spatial position of accessory parts such as local coils through example can be established by markings and assigned attenuation values on the basis of a database.

The known methods operate relatively satisfactorily as such. However each of the known methods is restricted and thus not suitable for complete definition of attenuation maps. Thus for example either the attenuation values of bones or of local coils can be determined with the known methods.

SUMMARY

In at least one embodiment of the present invention, an improved method is specified for defining an attenuation map.

In accordance with an example embodiment of the invention a method for defining an attenuation map is specified, comprising:
  Creating at least two data sets from which attenuation values are able to be determined,
  Evaluating the data sets and determining attenuation values,
  Weighting the attenuation values determined and
  Creating the attenuation map by combining the weighted attenuation values.

As a result of the use of that least two data sets for determining attenuation values it is possible to take account of the various materials present. The weightings of the attenuation values determined before they are combined into the attenuation map especially allow the relevance of the materials to be taken into account. The more data sets are used for determining the attenuation values the more accurate will be the attenuation map. The data sets for determining the attenuation values can for example be determined with the methods already known. In such cases those methods are used in particular which are able to represent different materials or tissue respectively of a patient in such a way that attenuation values are able to be determined. Frequently it is sufficient to merely identify the materials depending on the location and then to insert the attenuation values of the respective material known per se.

Each of the data sets preferably covers a three-dimensional mapping volume able to be divided up into volume elements. Attenuation values are determined for each of the volume elements. This makes it easier to apply the attenuation map to a measured PET data set which will generally be present in the same coordinate system as the attenuation map.

In an advantageous embodiment of invention the weighting of the attenuation values comprises the following:
  For each attenuation value of each volume element determined at least one weighting factor is determined,
  Selection of the attenuation value with the highest weighting factor in each volume element and
  Multiplication of the respective attenuation value by the respective weighting factor.

In the event of each of the data sets covering the same imaging volume there are at least two attenuation values for each of the volume elements. In general however the attenuation value is determined will not exhibit the same quality within one data set. Thus for example one data set which was recorded with an MR sequence for displaying bones merely delivers attenuation values relevant in the volume elements in which bone tissue is present. In other volume elements in which soft tissue is present for example, the data set does not deliver any usable attenuation values. In these volume elements of the respective attenuation values would be assigned a weighting factor of "zero" so that these do not get into the attenuation map. The multiplication of the attenuation values determined by the allocated weighting factor also allows differences in the quality of the method used to be taken into consideration during the assembly of the attenuation map. It is thus possible for example for two different methods to be used for determining the two data sets, with the quality of the attenuation values determined from the data sets being at different levels, especially having differences in accuracy. The different levels of weighting factor for the two methods takes account of these circumstances in the multiplication of the respective attenuation value by the respective weighting factor.

In an alternate embodiment of the invention the weighting of the attenuation values comprises the following:
  At least one weighting factor is determined for each attenuation value of each volume element,
  Multiplication of the respective attenuation value by the respective weighting factor for each volume element and
  Averaging of the weighted attenuation values for each volume element.

In this embodiment of the invention all the attenuation values are included in the attenuation map. However after multiplication by the respective weighting factor they are combined as average values and inserted into the attenuation map.

In an advantageous embodiment of the invention a neural network is used for weighting the attenuation values, the input nodes of which correspond in each case to a volume element and the weighting factors have been added to the neural network by training with example data sets. The use of the neural network is an especially simple realization option for determining the eventual attenuation map and for weighting values. The training can typically be undertaken by so-called back propagation.

An embodiment of the invention is especially advantageous in that each of the data sets is evaluated with that least two evaluation methods for determining the attenuation values. This increases the accuracy of the attenuation values determined.

In an advantageous embodiment of the invention at the least two weighting factors are used in the weighting of the least one of the weighting values. In this case a first of the weighting factors preferably reflects a certainty of the method used for determining the attenuation value. A second off the weighting factors reflects a material-specific certainty of the method used. Using different weighting factors allows method-dependent uncertainties in the definition of the attenuation values to be taken into consideration. This takes account of the fact that attenuation values of different quality are able to be determined by way of the known methods. In such cases a merely method-dependent certainty or reliability of the method is able to be taken into account by the first weighting factor, while the second weighting factor also takes into account the material present in the respective volume element in relation to the method used. Bones can thus be detected with a high level of certainty with a known method for example. The first weighting factor for this method would be accordingly high.

All attenuation values of volume elements in which bone tissue was identified will be allocated high values of the second weighting factor, while the remaining volume elements will be allocated a lower second weighting factor or the weighting factor 0. When other MR technologies are used for example, soft tissue can be displayed. However different soft tissue is only able to be differentiated with difficulty. This method already offers a low certainty or reliability so that the first weighting factor must be small. Despite this the areas with a sufficiently strong and signal our certain differentiation of tissue to be undertaken so that the corresponding volume elements can be allocated a high second weighting factor. By contrast volume elements which lie in areas with low MR signal are only allocated a low second weighting factor.

BRIEF DESCRIPTION OF THE DRAWINGS

Further advantages and embodiments of the invention emerge from the example embodiments described below in conjunction with the figures. The figures show:

FIG. 2 a schematic flowchart of an embodiment of the invention.

DETAILED DESCRIPTION OF THE EXAMPLE EMBODIMENTS

Figure 1:
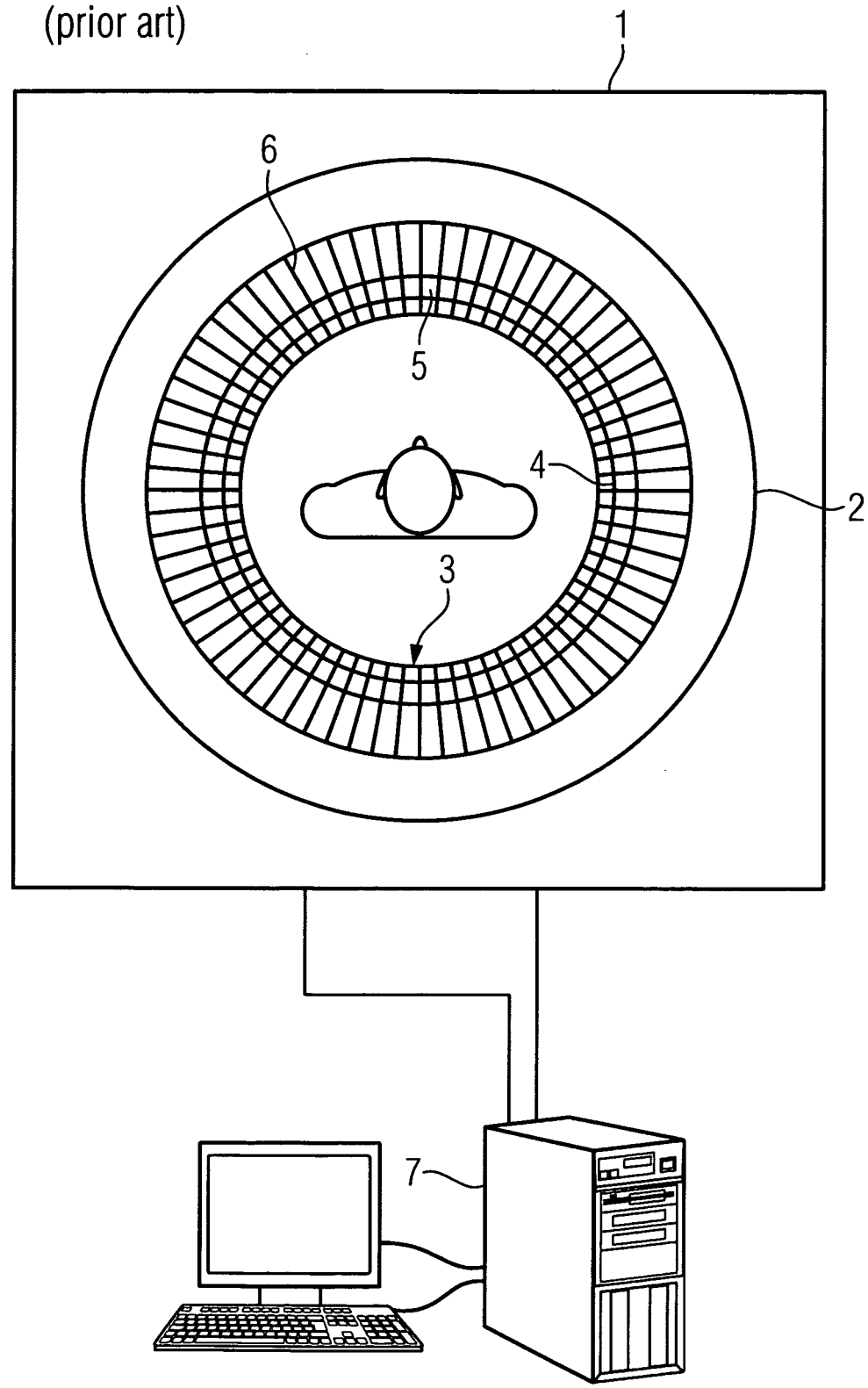
FIG. 1 a schematic diagram of an MR-PET device.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used in a combined MR-PET device. A combined device has the advantage that both MR and also PET data can be obtained isocentrically. This makes it possible to precisely define the examination volume within the region of interest with the data of the first modality (PET) and to use this information in the further modality (e.g. magnetic resonance). A transmission of the volume information of the region of interest from an external PT device to an MR device is possible; however it results in an increased effort for registration of the data. In general all data able to be defined with magnetic resonance or other imaging methods can be determined on the selected region of interest in the PET data set. For example instead of the spectroscopy data, fMRI data, diffusion maps, T1 or T2-weighted images or quantitative parameter maps can be obtained by means of magnetic resonance examinations in the region of interest. Likewise methods of computer tomography (e.g. perfusion measurement, multiple energy imaging) or x-rays can be employed. The advantage of the method described is in each case that the region of interest can be narrowed very explicitly by way of the PET data set to a specifically present pathology of the patient.

In addition however it is also possible, by using a number of so-called tracers, to display different biological characteristics in the PET data set and thus further optimize the region of interest and the volume defined by said region immediately, which is then analyzed in subsequent examinations.

FIG. 1 shows a known facility for overlaid MR and PET image display. The facility 1 consists of a known MR tube 2. The MR tube 2 defines a longitudinal direction z, which extends orthogonally to the plane of the drawing of FIG. 1.

As is shown in FIG. 1, arranged coaxially within the MR tubes 2 are a number of PET detection units 3 lying in pairs opposite each other around the longitudinal direction z. The PET detection units 3 preferably consist of an APD photodiode array 5 with an upstream array of LSO crystals 4 and an electrical amplifier circuit (AMP) 6. Embodiments of the invention are not however restricted to the PET detection units 3 with the APD photodiode array 5 and the upstream array made of LSO crystals 4, but other types of photodiode, crystals and apparatus can equally well be used for detection.

The image processing for superimposed MR and PET image presentation is undertaken by a computer 7.

Along their longitudinal direction z, the MR tubes define a cylindrical first field of vision. The plurality of PET detection units 3 define along the longitudinal direction z a cylindrical second field of vision. Inventively the second field of vision of the PET detection units 3 essentially corresponds to the first field of vision of the MR tubes 2. This is realized by a corresponding adaptation of the arrangement density of the PET detection units 3 along the longitudinal direction z.

FIG. 2 shows a schematic flowchart of a preferred embodiment of the invention. In this case a number of three-dimensional data sets is initially determined using different methods of measurement. FIG. 2 shows the data sets 101a, 101b and 101c by way of example. Within the data sets 101a, 101b and 101c and the imaging volume able to be broken down into volume elements is covered, in which a later PET measurement will also be undertaken. To determine attenuation values there are a number of methods available of which the methods 103a, 103b and 103c are shown by way of example. In this case it is possible for individual sets of the data sets 101a, 101b and 101c to be able to be evaluated with a number of the methods 103a, 103b and 103c and for attenuation values to be able to be determined. In FIG. 2 the data set 101a is evaluated by means of the methods 103a and 103b, which is shown by the arrows 105. The data set 101b is only evaluated with the method 103b, which is shown by the arrow 107. The data set 101c is only evaluated by way of the method 103c, which is shown by the arrow 109.

The methods 103a, 103b and 103c in each case deliver results in the form of attenuation values which are combined into result data sets 111a, 111b and 111c. The result data sets 111a, 111b and 111c correspond in each case to the data sets 101a, 101b and 101c and containing the entire tea of the attenuation value is determined from the data sets 101a, 101b and 101c.

The result data sets 111a, 111b and 111c are subjected to an evaluation 113, through which an attenuation map 115 is generated.

Data sets 101a, 101b and 101c are preferably created with different methods. These can be methods in which different MR sequences are used for example. Likewise data sets can be used which had been measured by three-dimensional surface scanners. In addition position sensors can for example be built into accessory parts such as local coils, which also deliver data sets to enable an attenuation map of the respective accessory parts to be created. Through the evaluation of the data sets 101a, 101b and 101c attenuation values for each volume element will be determined. Simultaneously the evaluation methods deliver confidence values which will be used for weighting the respective attenuation values. In this case the confidence value can be a different size for each volume element of the imaging volume, whereby specificity for displaying individual material classes and tissue types of the selected method used in each case is taken into account. In such cases volume elements are allocated a high confidence value for which the aid of the method used there is a high probability that the correct material has been recognized. Volume elements for which the respective method cannot provide any information or only unreliable information about the attenuation values will be allocated a low confidence value.

With Atlas-based methods of determining attenuation values the confidence of values can be determined as the atlas is being created and can be integrated into this. In such cases volume elements which exhibit a high variability between the data sets used to create the Atlas are allocated a low confidence, those with low variability are allocated a high confidence value. The assignment of attenuation values from the Atlas then goes hand-in-hand with the allocation of the corresponding confidence values. Only volume elements of which the composition is highly likely to be identical during the creation of the Atlas and the creation of the data set to be evaluated are given a high confidence value, for example bones. Volume elements which are generally subjected to changes such as the inside of the bowel for example, are allocated a low confidence value. In the final weighting of the attenuation values the respective attenuation values are multiplied by their confidence values and either the attenuation values with the highest confidence value for the respective volume element are entered into the attenuation map or all attenuation values determined, multiplied in each case by their confidence value, are averaged and transferred into the attenuation map.

In such cases it is possible for the weighting factors to be entered by the user or predetermined by the manufacturer of the device on which the method is implemented. In addition it is possible for the functions for determining the confidence values to be predetermined by the user or already implemented by the manufacturer. These functions are generally produced from the method used for determining the attenuation values.

Preferably a neural network is used for determining the attenuation map and weighting of the individual attenuation values of the respective volume element, with the input nodes of said network each corresponding to one volume element of the data set. The weighting factors are defined by training the network with the example data sets. Back propagation can typically be used in such cases. It is of advantage for the individual data sets, before their processing, to be transformed in such a way that they are present in a uniform reference coordinate system. This can be done through example by scaling, interpolation as well as rigid or non-rigid transformations such as a drawing correction for example.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating an attenuation map, comprising:
   creating, by an image processing device, at least two data sets from which attenuation values are determinable;
   evaluating the created at least two data sets and determining attenuation values;
   weighting the determined attenuation values; and
   creating the attenuation map by combining the weighted attenuation values.

2. The method as claimed in claim 1, wherein each of the at least two data sets covers a three-dimensional imaging volume dividable into volume elements.

3. The method as claimed in claim 2, wherein attenuation values are determined for each of the volume elements.

4. The method as claimed 3, wherein the weighting of the attenuation values comprises:
   determining, for each attenuation value of each volume element determined, at least one weighting factor;
   selecting, for each volume element, the attenuation value with the highest weighting factor; and
   multiplying respective attenuation values by respective weighting factors.

5. The method as claimed 4, wherein the weighting of the attenuation values comprises:
   determining, for each determined attenuation value of each volume element, at least one weighting factor;
   multiplying a respective attenuation value by the determined weighting factor for each volume element; and
   averaging the weighted attenuation values for each volume element.

6. The method as claimed 5, wherein a neural network is used for weighting the attenuation values of the volume elements, with the input nodes of said network each corresponding to one of the volume elements and the weighting factors being added to the neural network by training with example data sets.

7. The method as claimed 3, wherein the weighting of the attenuation values comprises:
   determining, for each determined attenuation value of each volume element, at least one weighting factor;
   multiplying a respective attenuation value by the determined weighting factor for each volume element; and
   averaging the weighted attenuation values for each volume element.

8. The method as claimed 7, wherein a neural network is used for weighting the attenuation values of the volume elements, with the input nodes of said network each corresponding to one of the volume elements and the weighting factors being added to the neural network by training with example data sets.

9. The method as claimed in claim 1, wherein at least two weighting factors are used for the weighting of at least one of the attenuation values.

10. The method as claimed in claim 9, wherein a first of the weighting factors reflects a reliability of the method used for determining the attenuation value.

11. The method as claimed in claim 10, wherein a second of the weighting factors reflects a material-specific reliability of the method used.

12. The method as claimed in claim 1, wherein a first of the at least two data sets is created by way of magnetic resonance tomography.

13. The method as claimed in claim 12, wherein a second of the at least two data sets is created by way of a surface scanner.

14. The method as claimed in claim 1, wherein each of the at least two data sets is evaluated with at least two evaluation methods for determining the attenuation values.

15. The method as claimed in claim 1, wherein the at least two data sets are created by way of two different methods, with each of the methods being suitable for determining the attenuation values of different materials.

16. The method as claimed in claim 1, wherein the at least two data sets are transformed for evaluation such that they contain a uniform reference coordinate system.

17. A non-transitory computer readable medium including program segments for, when executed on a computer device, causing the computer device to implement the method of claim 1.

* * * * *